United States Patent
Gualtieri et al.

(10) Patent No.: US 12,207,992 B2
(45) Date of Patent: *Jan. 28, 2025

(54) TRANSVERSELY EXTENSIBLE CONTINUOUS ELASTIC LAMINATE, AND A METHOD FOR PRODUCING THE SAME

(71) Applicant: Fameccanica.Data S.p.A., San Giovanni Teatino (IT)

(72) Inventors: Diego Gualtieri, San Giovanni Teatino (IT); Alessandro Cipriani, San Giovanni Teatino (IT)

(73) Assignee: Fameccanica.Data S.p.A., San Giovanni Teatino Chieti (IT)

( * ) Notice: Subject to any disclaimer, the term of this patent is extended or adjusted under 35 U.S.C. 154(b) by 234 days.

This patent is subject to a terminal disclaimer.

(21) Appl. No.: 17/696,998

(22) Filed: Mar. 17, 2022

(65) Prior Publication Data
US 2022/0296431 A1    Sep. 22, 2022

(30) Foreign Application Priority Data

Mar. 19, 2021 (EP) .................................... 21163723

(51) Int. Cl.
*A61F 13/15* (2006.01)
*A61F 13/49* (2006.01)
(Continued)

(52) U.S. Cl.
CPC .. *A61F 13/15593* (2013.01); *A61F 13/15699* (2013.01); *A61F 13/4902* (2013.01);
(Continued)

(58) Field of Classification Search
CPC .......... A61F 13/15593; A61F 13/15699; A61F 13/4902; A61F 2013/49033;
(Continued)

(56) References Cited

U.S. PATENT DOCUMENTS

| 5,399,219 A | * | 3/1995 | Roessler | ................. A61F 13/58 |
| | | | | 156/271 |
| 2004/0016499 A1 | * | 1/2004 | Miyamoto | .............. A61F 13/58 |
| | | | | 156/66 |

(Continued)

FOREIGN PATENT DOCUMENTS

| EP | 3213728 A1 | 9/2017 |
| WO | 2021001492 A1 | 1/2021 |

OTHER PUBLICATIONS

Chinese Office Action issued in counterpart Chinese application dated Jun. 3, 2023.
European Search Report and Opinion dated Sep. 17, 2021. 5 pages.

*Primary Examiner* — George R Koch
*Assistant Examiner* — Christopher C Caillouet
(74) *Attorney, Agent, or Firm* — RMCK Law Group PLC

(57) ABSTRACT

A transversely extensible continuous elastic laminates includes a continuous elastic tape sandwiched between two continuous webs, and at least one row of tabs extending transversely outside the two webs, wherein the tabs are made of a non-woven material and have respective micro-hook pads integrally formed in the non-woven material forming the tabs and completely surrounded by a portion of a flat surface of the respective tabs.

7 Claims, 12 Drawing Sheets

(51) Int. Cl.
  *B32B 5/04*    (2006.01)
  *B32B 7/05*    (2019.01)
  *B32B 37/14*   (2006.01)
  *B32B 38/00*   (2006.01)

(52) U.S. Cl.
  CPC ................. *B32B 5/04* (2013.01); *B32B 7/05* (2019.01); *B32B 37/14* (2013.01); *B32B 38/0004* (2013.01); *B32B 38/1875* (2013.01); *A61F 2013/49033* (2013.01); *B32B 2307/51* (2013.01); *B32B 2555/02* (2013.01)

(58) Field of Classification Search
  CPC .. A61F 13/15756; A61F 13/62; A61F 13/622; A61F 13/15577; A61F 13/15723; A61F 13/15764; A61F 13/56; A61F 2013/15821; B32B 5/04; B32B 7/05; B32B 37/14; B32B 38/0004; B32B 38/1875; B32B 2307/51; B32B 2555/02; B32B 3/08; B32B 3/28; B32B 5/022; B32B 5/26; B32B 27/00; B32B 27/12; B32B 37/00; B32B 2555/00
  See application file for complete search history.

(56) References Cited

U.S. PATENT DOCUMENTS

| | | | |
|---|---|---|---|
| 2005/0256495 A1* | 11/2005 | Schlinz | A61F 13/5633 |
| | | | 604/385.01 |
| 2018/0037020 A1* | 2/2018 | Bonelli | B32B 7/05 |
| 2022/0233366 A1* | 7/2022 | Picot | B32B 27/302 |

* cited by examiner

TRANSVERSELY EXTENSIBLE CONTINUOUS ELASTIC LAMINATE, AND A METHOD FOR PRODUCING THE SAME

CROSS-REFERENCE TO RELATED APPLICATION

This application claims priority to European Patent Application No. 21163723.6 filed Mar. 19, 2021. The disclosure of the above application is incorporated herein by reference in its entirety.

FIELD OF THE INVENTION

The present invention relates to a transversely extensible continuous elastic laminate.

The present invention has been developed with particular reference to the production of disposable absorbent sanitary articles, such as, for example, diapers, training pants, absorbent sanitary products for incontinent adults, etc.

A transversely extensible continuous elastic laminate may constitute a semi-finished intermediate product which can be used for supplying machines for manufacturing absorbent sanitary articles. The transversely extensible continuous elastic laminate can be cut transversely to produce elastic side panels for absorbent sanitary articles. Discrete left and right fastening tabs could be already attached externally on the elastic laminate.

Embodiments of the present invention also relate to an elastic side panel for absorbent sanitary articles.

The present invention also relates to methods for producing transversely extensible continuous elastic laminates.

PRIOR ART

An absorbent sanitary article wearable as a pant typically has a structure that comprises a rectangular-shaped central body or chassis and at least one pair of elastic side panels which extend laterally from opposite sides of the central body in the front or rear section of the central body. The side panels are provided with fastening tabs, typically comprising micro-hooks pads, which can be releasably attached to a front panel for closing the absorbent sanitary article around the waist of the user.

EP-A-3213728 discloses a transversely extensible elastic laminate comprising: a first and a second web, having respective pleated central portions, an elastic tape sandwiched between the pleated central portions of the first and second web and elastically stretchable in a transverse direction, and a plurality of fastening tabs spaced apart from each other in a longitudinal direction.

The fastening tabs each include a non-woven support web of soft material and a micro-hook pad of relatively rigid thermoplastic material fixed on a surface of the non-woven support web by glue or by welding.

The micro-hook pads are produced starting from continuous tapes, usually made of relatively rigid thermoplastic material, having continuous or intermittent micro-hook formations integrally formed thereon. The continuous tape with integrally formed micro-hook formations is cut to form a plurality of discrete micro-hook pads. Such discrete micro-hook pads are spaced by a desired pitch and are fixed in spaced positions on a surface of a continuous non-woven support web. The continuous non-woven support web with the micro-hook pads fixed thereon is then cut to form fastening tabs each including a non-woven support web of soft material and a micro-hook pad of relatively rigid thermoplastic material fixed on a surface of the non-woven support web by glue or by welding.

The continuous tapes with integrally formed micro-hook formations is manufactured by suppliers specialized in manufacturing hook-and-loop fasteners. The micro-hook tapes are packaged in reels which are delivered to the manufacturing plants of absorbent sanitary articles. In the machines for manufacturing absorbent sanitary articles the reels of continuous tapes with integrally formed micro-hook formations are unwound, cut, spaced, and fixed to the continuous non-woven support web. All these operations require complex and expensive dedicated equipment which increase the complexity of the machines for manufacturing absorbent sanitary articles. The cost of the continuous tapes with integrally formed micro-hook formations is high, therefore, the dimensions of the micro-hook pads or patches is kept to the minimum possible, which requires complex equipment for cutting the continuous tapes with integrally formed micro-hook formations in very small pieces and for feeding such small pieces with high precision to the continuous non-woven support web.

A further drawback of the prior art is that the micro-hook fastening pads extend for the whole width of the support tape, i.e., the lateral edges of the micro-hook pads are aligned to the lateral edges of the support web. When touching the fastening tab, the user perceives a sharp feeling due to the fact that the rigid micro-hook pads extend up to the edges of the fastening tab. This structure of the fastening tabs gives rise to an unpleasant stiffness and sharpness perception during the application of the sanitary article to the wearer. It is not unusual that the user gets scratches or small cuts on the soft skin under the nails due to the contact with sharp and rigid edges of the micro-hook pads.

OBJECT AND SUMMARY OF THE INVENTION

The object of the present invention is to provide a transversely extensible continuous elastic laminate usable to produce elastic side panels for absorbent sanitary articles, which overcomes the problem of the prior art.

According to a first aspect of the invention, this object is achieved by a transversely extensible continuous laminate having the features of claim 1.

An important feature of the present invention is that the tabs with micro-hook pads can be manufactured in-line in a machine for manufacturing absorbent sanitary articles starting from reels of non-woven material. Therefore, there is no need to supply the machine for manufacturing absorbent sanitary articles with reels of micro-hook tapes supplied by companies specialized in manufacturing hook-and-loop fasteners.

The present invention eliminates handling and transportation of micro-hook tapes, which reduces costs, simplifies handling of raw material in the plants for manufacturing absorbent sanitary articles, and has a positive impact on sustainability due to the elimination of the need of transporting the micro-hook tapes.

According to another aspect, the present invention relates to an elastic side panel for absorbent sanitary articles having the features of claim 6.

According to another aspect, the invention relates to methods for producing transversely extensible laminates.

The manufacturing methods, as compared to the prior art, provide a better control on the distance between the fastening tabs, which in the method according to the invention are not applied as discontinuous discrete elements. This reduces manufacturing wastes and has a direct positive impact on sustainability.

The claims form an integral part of the technical disclosure provided here in relation to the invention.

BRIEF DESCRIPTION OF THE DRAWINGS

The present invention will now be described with reference to the attached drawings, provided purely by way of non-limiting example, wherein.

In the following description, identical or similar components will be indicated by the same reference numerals.

It should be appreciated that the attached drawings are schematic and not to scale with respect to real products. Various figures may not be represented in the same scale. Also, in various figures some elements may not be shown to better show other elements.

DETAILED DESCRIPTION

FIGS. 1-10 schematically show various steps of a method for producing a transversely extensible continuous elastic laminate.

Figure 1:
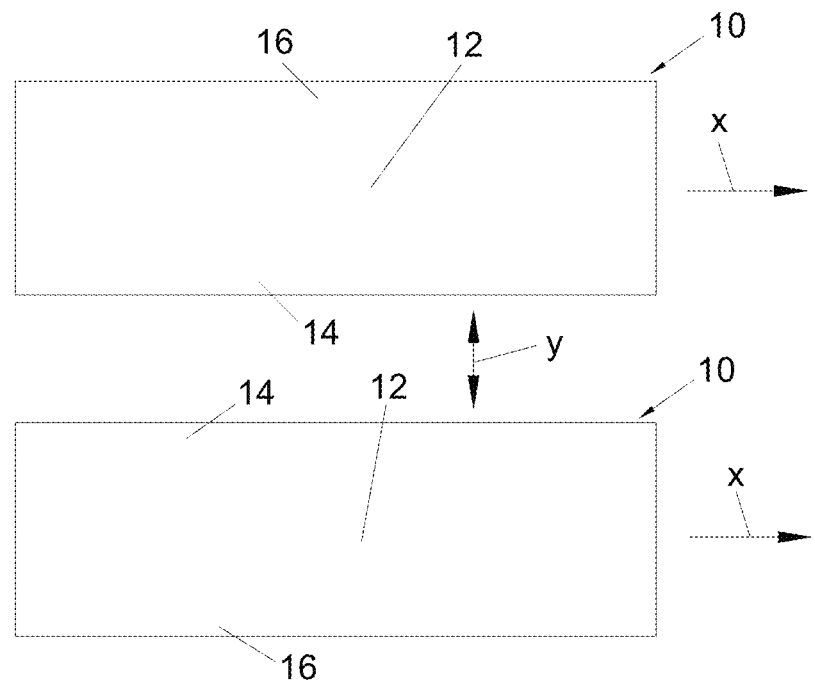
FIGS. 1-10 are schematic views showing various steps of a first embodiment of a method for producing a transversely extensible continuous elastic laminate having integral micro-hook pads.

In a first step, shown in FIG. 1, two first continuous webs 10 are fed in a longitudinal direction X. The two first continuous webs 10 may be made of a non-woven material. In a possible embodiment, the two first continuous webs 10 may be obtained from a single continuous web unwound from a reel and cut longitudinally so as to form two separate webs advancing in the longitudinal direction X.

The two first continuous webs 10 are spaced apart from each other in a transversal direction Y orthogonal to the longitudinal direction X.

Each of the two first continuous webs 10 has a central portion 12 and first and second edge portions 14, 16 opposite to each other with respect to the central portion 12.

The two first continuous webs 10 may be positioned on the outer surface of a wheel or on the upper surface of a conveyor belt as they advance continuously in the longitudinal direction X.

Figure 2:
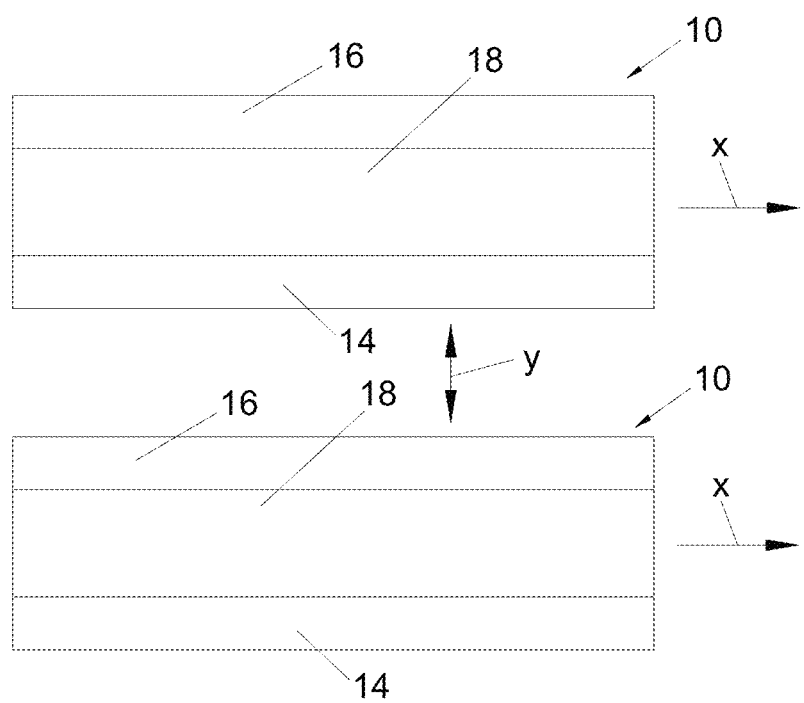

In a second step, shown in FIG. 2, two continuous elastic tapes 18 are fed in the same longitudinal direction X and are overlapped to the respective central portions 12 of the two first continuous webs 10. The two elastic tapes 18 may be obtained from a single continuous elastic tape unwound from a reel and cut longitudinally so as to form the two separate elastic tapes advancing in the longitudinal direction X.

The two elastic tapes 18 are elastically stretched in the transversal direction Y when they are applied to the respective central portions 12 of the two continuous webs 10. The two continuous elastic tapes 18 may have the capability to extend in the transversal direction Y by at least 100%, and preferably by 300%, with respect to the respective rest dimensions and to return to the respective rest dimensions in the absence of a transversal force. In a possible embodiment, the degree of transversal elastic stretching of the two continuous elastic tapes 18 may be in the order of 200%. This means that the two continuous elastic tapes 18 are applied on the respective first continuous webs 10 with a width essentially equal to three times the width that the continuous elastic tapes 18 have at rest, i.e., in the absence of transversal forces.

The transverse extension of the two continuous elastic tapes 18 may be obtained by a spreading device comprising, for each continuous elastic tape 18, two wheels with respective axes inclined with respect to each other, as disclosed in EP-A-3213728.

The transversely stretched continuous elastic tapes 18, once applied to the respective central portions 12 of the two first continuous webs 10 may be retained in the stretched state by vacuum suction, as disclosed in EP-A-3213728.

In a possible embodiment, the continuous elastic tapes 18 may have different widths in the transverse direction Y and/or may be stretched in said transverse direction Y to reach different widths.

Figure 3:
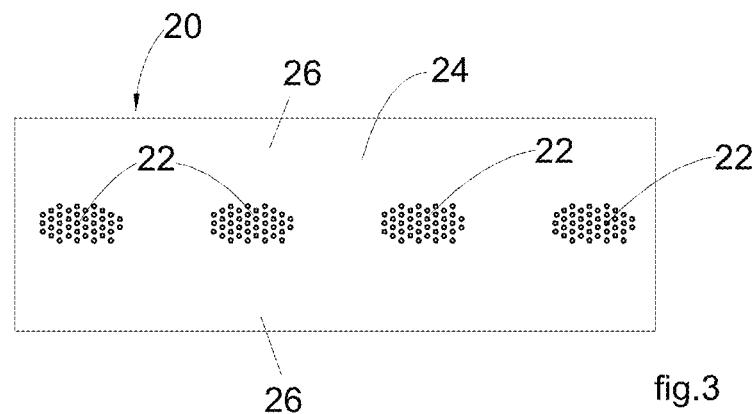

With reference to FIG. 3, the method comprises providing a continuous support web 20 made of a non-woven material and having a row of micro-hook pads 22 integrally formed on a planar surface 24 of the support web 20.

The continuous support web 20 has two continuous longitudinal edge portions 26 and the row of micro-hook pads 22 is located in a central portion of the support web 20. The micro-hook pads 22 are spaced apart from each other in the longitudinal direction X.

In a possible embodiment, the micro-hook pads 22 may have the respective micro-hooks alternately oriented in opposite directions, so that in each pair of adjacent micro-hook pads 22 the micro-hooks of one pad 22 are oriented in a direction opposite with respect to the micro-hooks of the other pad 22.

Figure 4:
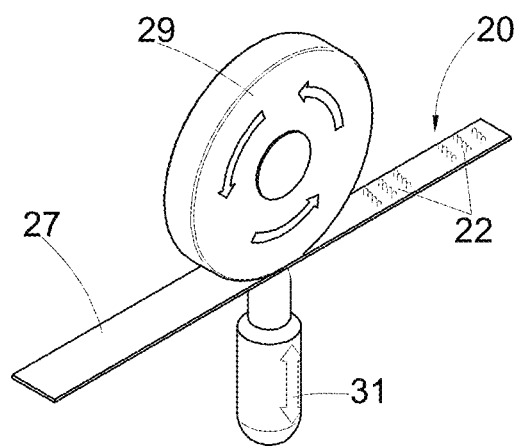

The continuous support web 20 with the integrally formed micro-hook pads 22 may be formed as disclosed in detail in WO2010/085492 A1 and as shown schematically in FIG. 4. With reference to FIG. 4, a smooth non-woven web 27 passes through a micro-hook forming unit 28. The micro-hook forming unit 28 may comprise a molding roller 29 having a plurality of cavities and a ultrasonic horn 31 which compresses the non-woven web 27 against the surface of the molding roller 29.

The vibrating energy produced by the ultrasonic horn 31 liquifies or fluidifies locally the non-woven material of the non-woven web 27, which penetrates in a fluid or liquid state in the cavities of the molding roller 29. The material of the non-woven web 27 which penetrates in the cavities of the molding roller 29 after cooling forms micro-hook pads 22 integral with the non-woven material. At the exit of the micro-hook forming unit 28 a continuous support web 20 is formed having a row of integral micro-hook pads 22.

The discrete micro-hook pads 22 may be obtained by providing on the molding roller 29 an intermittent pattern of cavities. Alternatively, the molding roller 29 may have a continuous pattern of cavities and the discrete micro-hook pads 22 may be formed by intermittently stopping the power supplied to the ultrasonic horn 32. As a further alternative, the molding roller 29 may have a continuous pattern of cavities and the discrete micro-hook pads 22 may be formed by intermittently detaching the ultrasonic horn 32 from the molding roller 29.

Figure 5:
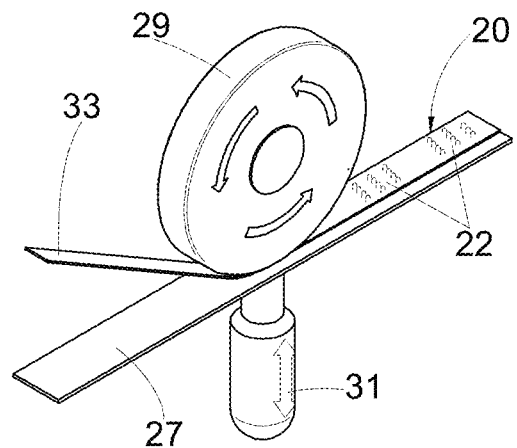

With reference to FIG. 5, in a possible embodiment, an additional web 33 may be applied on the central portion of the non-woven web 27 before passing the non-woven web 27 through the micro-hook forming unit 28. The additional web 33 may be a thermoplastic film or a non-woven web of a material different or identical to the material of the non-woven web 27. After passing through the micro-hook forming unit 28 the additional web 33, the micro-hook pads 22 and the non-woven web 27 form an integral structure.

In a possible embodiment, the micro-hook forming unit 28 may be a thermomechanical forming unit, in which the material of the non-woven web 27 is locally liquified or fluidified by heating and compression.

Figure 6:
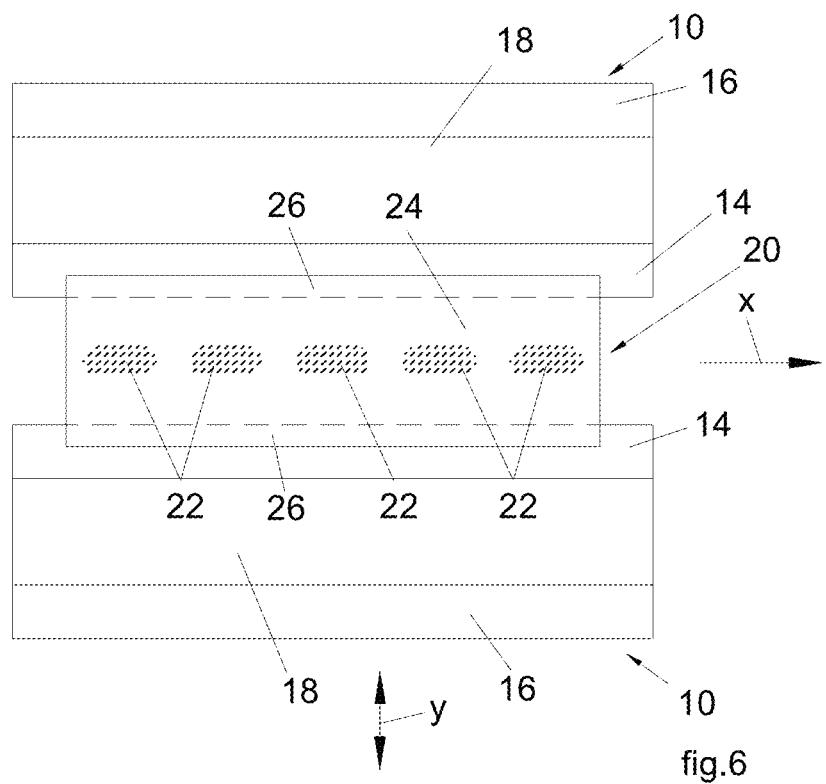

With reference to FIG. 6, the continuous support web 20 with integrally formed micro-hook pads 22 is fed in the longitudinal direction X and the two continuous longitudinal edge portions 26 of the support web 20 are overlapped to respective first edge portions 14 of the two first continuous webs 10. The two continuous longitudinal edge portions 26 of the continuous support web 20 may be retained on the respective edge portions 14 of the two first continuous webs 10 by the same vacuum suction which holds the stretched elastic tapes 18 on the first webs 10.

Figure 7:
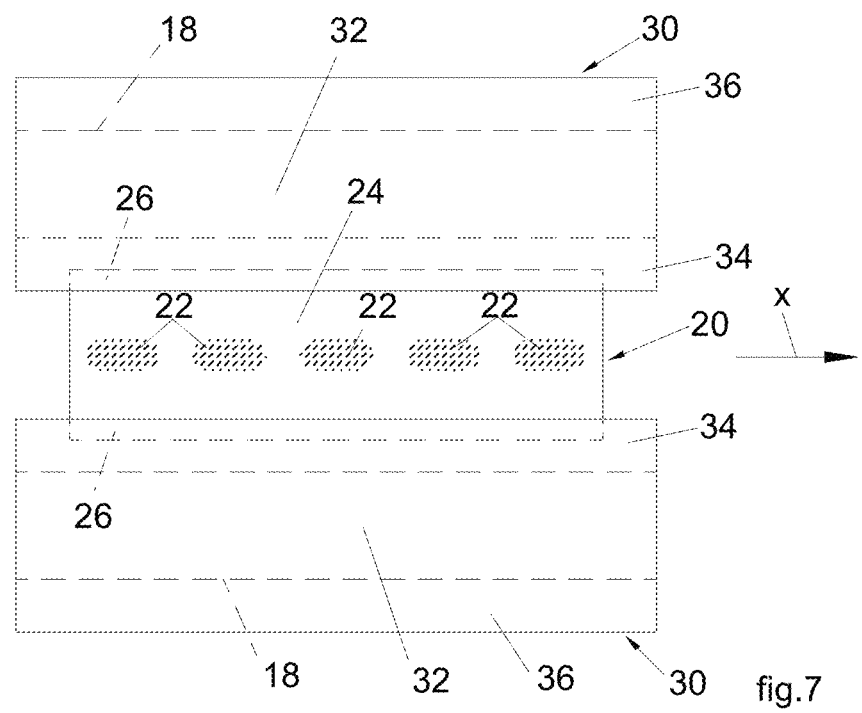

As shown in FIG. 7, in a further step two second continuous webs 30 are fed in the longitudinal direction Y, and are overlapped to the respective first continuous webs 10.

In a possible embodiment, the two second continuous webs 30 may be obtained from a single continuous web unwound from a reel and cut longitudinally so as to form two separate webs advancing in the longitudinal direction X.

The two second continuous webs 30 are spaced from each other in the transverse direction Y and have respective central portions 32 and respective first and second edge portions 34, 36 on opposite sides of the central portion 32. The two second continuous webs 30 may have the same width as the first continuous webs 10. The two second continuous webs 30 are applied over the respective first continuous webs 10 so that the two continuous elastic tapes 18 are sandwiched between the respective central portions 12, 32 of the first and second webs 10, 30. Also, the two continuous longitudinal edge portions 26 of the support web 20 are sandwiched between respective first edge portions 14, 34 of the two first and second continuous webs 10, 30.

Figure 8:
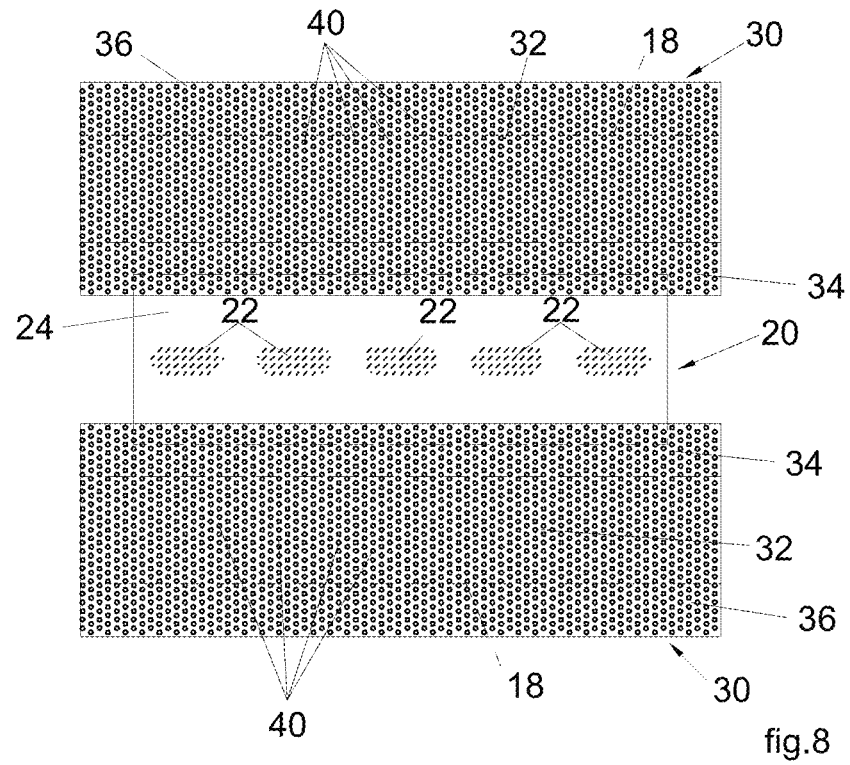

Then, as shown in FIG. 8, the two first and second webs 10, 30, the two elastic tapes 18 and the edge portions 26 of the support web 20 are fixed to each other by a pattern of spot welds 40. The spot welds 40 may be formed by ultrasonic welding as disclosed in EP-A-3213728. The pattern of spot welds 40 may have a reinforced area along the longitudinal portion connecting the first edge portions 14, 34 of the first and second webs to the edge portions 26 of the support web 20, in order to provide an increased joining strength in that area.

The elastic tapes 18 are stretched in the transversal direction Y during the spot welding which joins the elastic tapes 18 to the first and second webs 10, 30. The welding spots 40 may form through holes in the elastic tapes 18 in order to provide breathability features to the composite laminate, as disclosed in EP-A-3213728.

Figure 9:
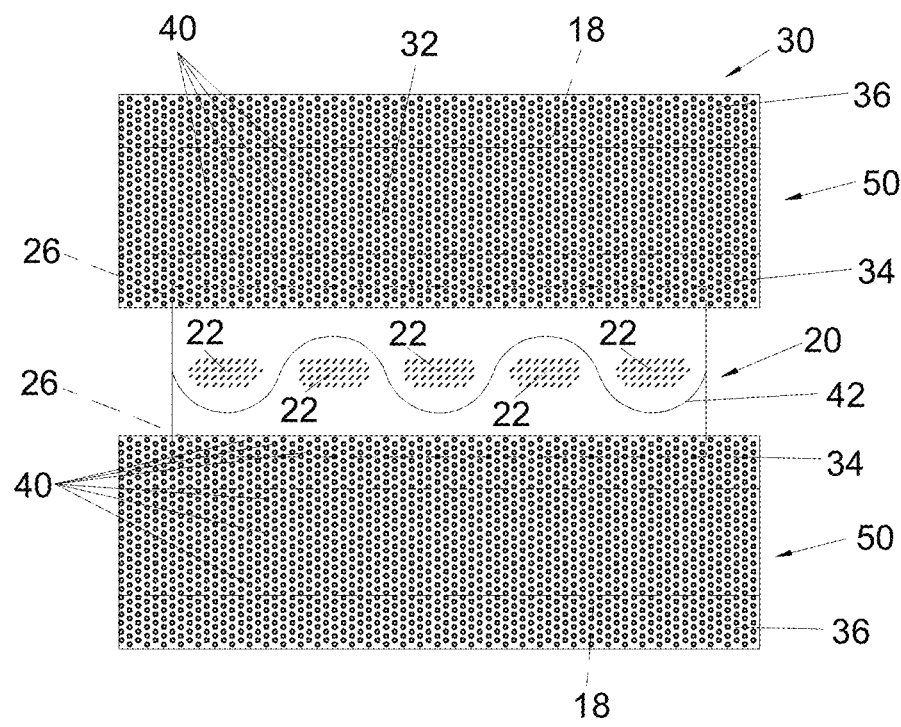

With reference to FIG. 9, the method further comprises a cutting step wherein the support web 20 is cut along a continuous undulated cutting line 42 passing between each pair of adjacent micro-hook pads 22. The continuous undulated cutting line 42 may be made by a cutting roller having a shaped cutting blade. The continuous undulated cutting line 42 is distanced from the edges of the micro-hook pads 22 so that each micro-hook pad 22 is completely surrounded by a portion of the planar surface 24 of the support web 20.

Figure 10:
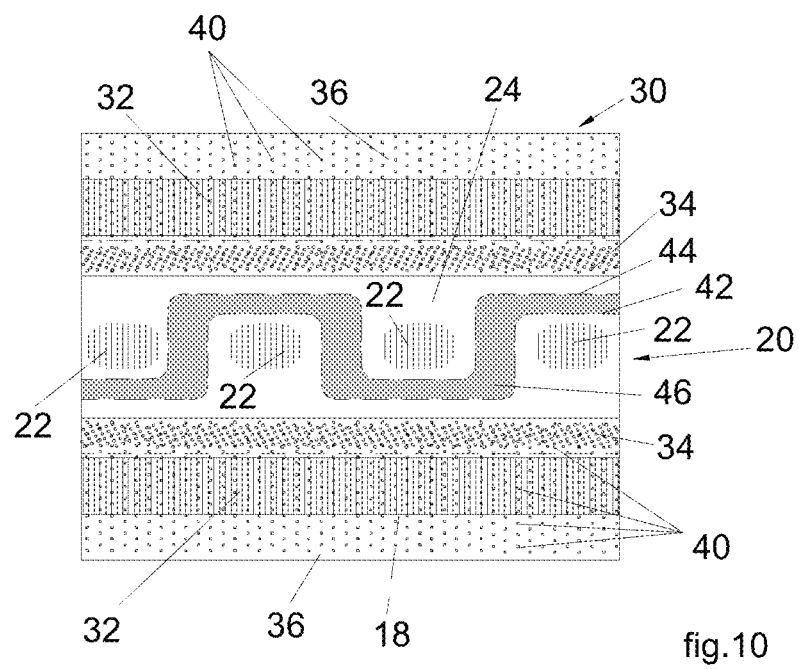

As shown in FIG. 10, in a possible embodiment, the support web 20 may be cut along two continuous undulated cutting lines 42, 44 passing between each pair of adjacent micro-hook pads 22. Two continuous undulated cutting lines 42, 44 define a continuous undulated strip 46 comprised between the two cutting lines 42, 44 which is disposed as waste.

The continuous undulated cutting line 42 or the continuous undulated cutting lines 42, 44 may pass at a distance from the edges of said micro-hook pads 22 comprised between 1-10 mm and preferably comprised between 2-7 mm.

Figure 11:
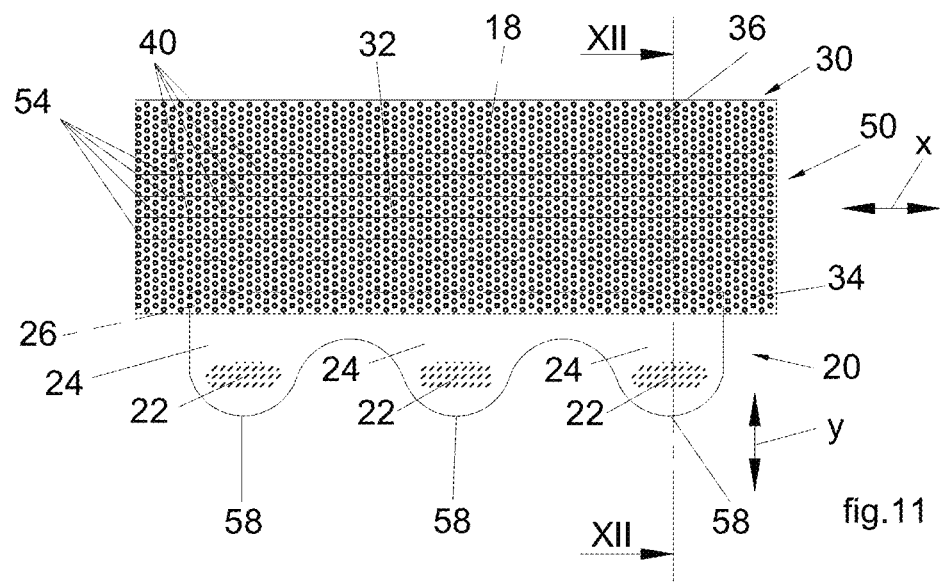
FIG. 11 is a schematic plan view of a transversely extensible continuous elastic laminate in an extended position.
Figure 12:
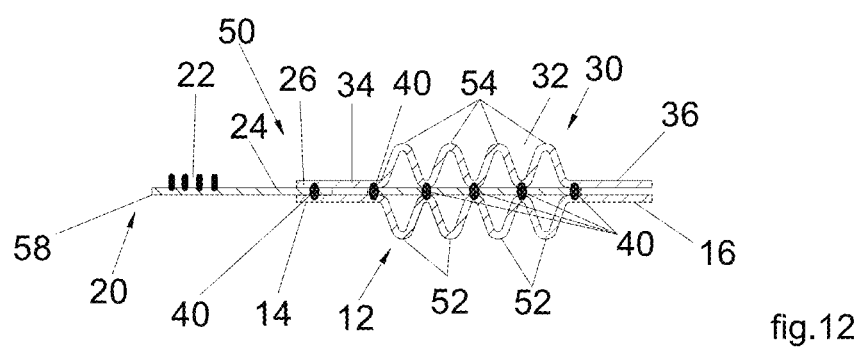
FIG. 12 is a schematic cross-section taken along the line XII-XII of FIG. 11.

After the cut of the support web 20 along the cutting line 42 or cutting lines 42, 44, two separate transversely extensible continuous elastic laminates 50 are formed, each of which has the form shown in FIGS. 11 and 12.

With reference to FIGS. 11 and 12, the transversely extensible continuous laminate 50 obtained by the previously disclosed method comprises a first and second continuous web 10, 30 extending along a longitudinal direction X and a continuous elastic tape 18 elastically extensible in a transversal direction Y and sandwiched between the central portions 12, 32 of the first and second continuous web 10, 30 and joined thereto by a pattern of spot welds 40.

When the vacuum suction which holds the elastic tape 18 stretched in the transversal direction Y is released, the elastic tape 18 contracts in the transversal direction Y. The transversal contraction of the elastic tape 18 forms longitudinal pleats 52, 54 on the central portions 12, 34 of the first and second continuous web 10, 30. The edge portions 14, 34 and 16, 36 of the first and second continuous webs 10, 30 which extend transversally beyond the elastic tape 18 remain non-pleated.

The transversely extensible continuous elastic laminate 50 comprises a support web 20 made of non-woven material, having a continuous longitudinal edge portions 26 which is joined to the first non-pleated edge portions 14, 34 of the first and second web 10, 30 by said pattern of spot welds 40.

The continuous longitudinal edge portion 26 of the support web 20 may be sandwiched between the first edge portions 14, 34 of the first and second web 10, 30. In a possible embodiment, the continuous longitudinal edge portion 26 of the support web 20 may be fixed on the outer surface of one of the non-pleated edge portions 14, 34 of the first and second web 10, 30.

The pattern of spot welds 40 may be reinforced in the area joining the first non-pleated edge portions 14, 34 of the first and second web 10, 30 and the continuous edge portion 26 of the support web 20.

The support web 20 includes a row of tabs 58 made of non-woven material which extend from the continuous longitudinal edge portion 26. The tabs 58 are connected to each other by the continuous edge portion 26 and are spaced apart from each other in the longitudinal direction X. Each tab 58 has a respective micro-hook pad 22 integrally formed on a planar surface 24 of the respective tab 58. The planar surface 24 of each of the tabs 58 has a portion which completely surrounds the respective micro-hook pad 22. In a possible embodiment the portion of the planar surface 24 which surrounds the respective micro-hook pad 22 may have a width greater than 2 mm. The width of each tab 58 along a line parallel to the direction X and passing through the respective micro-hook pad 22 should be at least 4 mm larger than the width of the micro-hook pad 20 along the same line (2 mm on each side of the micro-hook pad 20). The width of each tab 58 may be 100 mm larger than the width of the micro-hook pad 20. For instance, if the width of the micro-hook pad 20 is 50 mm, the width of the respective tab 58 may be comprised between 54 mm and 150 mm.

Figure 13:
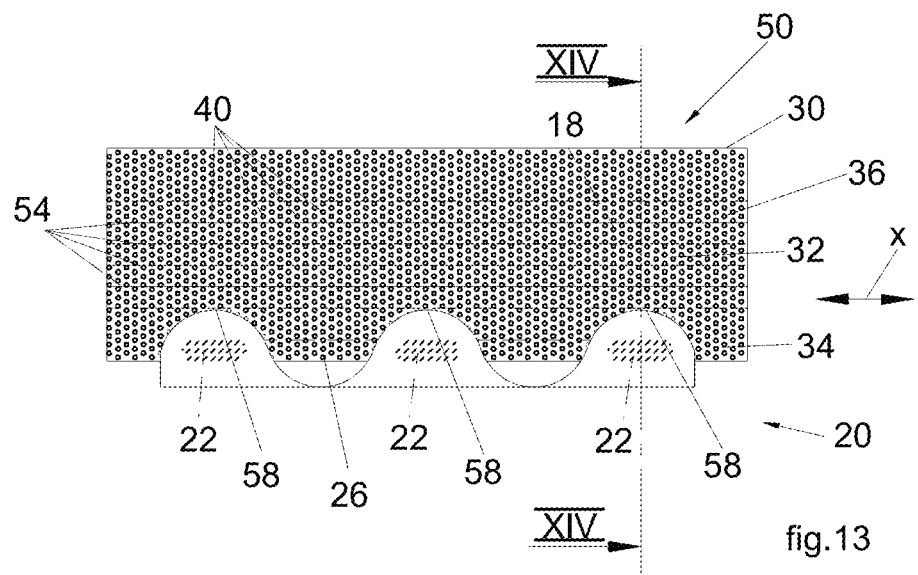
FIG. 13 is a schematic plan view showing the transversely extensible continuous elastic laminate of FIG. 11 in a folded configuration.
Figure 14:
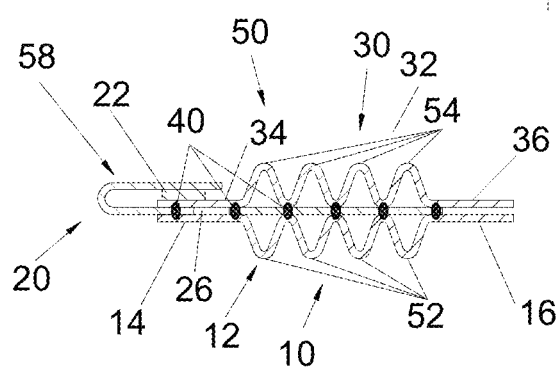
FIG. 14 is a schematic cross-section taken along the line XIV-XIV of FIG. 13.

With reference to FIGS. 13 and 14, the tabs 58 of the support web 20 may be folded over the second web 30 along a folding line parallel to the longitudinal axis X, so that the micro-hook pads 22 are releasably fastened to corresponding portions of the second web 30. Folding of the tabs 58 may be carried out before or after releasing the vacuum suction which keeps the elastic tape 18 stretched in the transverse direction Y. When the tabs 58 are folded as shown in FIGS. 10 and 11, the transversely extensible continuous elastic laminate 50 can be handled more easily without the risk that the micro-hook pads 22 engage with a non-woven web when the transversely extensible continuous elastic laminate 50 is wound in a reel or during the manufacturing process of absorbent sanitary products.

The transversely extensible continuous elastic laminate 50 is used for producing elastic side panels in machines for manufacturing absorbent sanitary articles. The transversely extensible continuous elastic laminate 50 may be formed in-line with respect to the manufacturing machine. In a possible embodiment, the transversely extensible continuous elastic laminate 50 can be wound in reels which can be stored before being delivered to a manufacturing machine.

In the machine for manufacturing absorbent sanitary products, the transversely extensible continuous elastic laminate 50 is cut along lines generally transversal to the longitudinal axis X for forming individual elastic side panels. The cutting lines which form the individual elastic side panels may have different shapes so as to form elastic side panels with the desired shape. The cuts which originate the individual elastic side panels are typically carried out while the tabs 58 of the transversely extensible continuous elastic laminate 50 are folded as shown in FIGS. 13 and 14.

Figure 15:
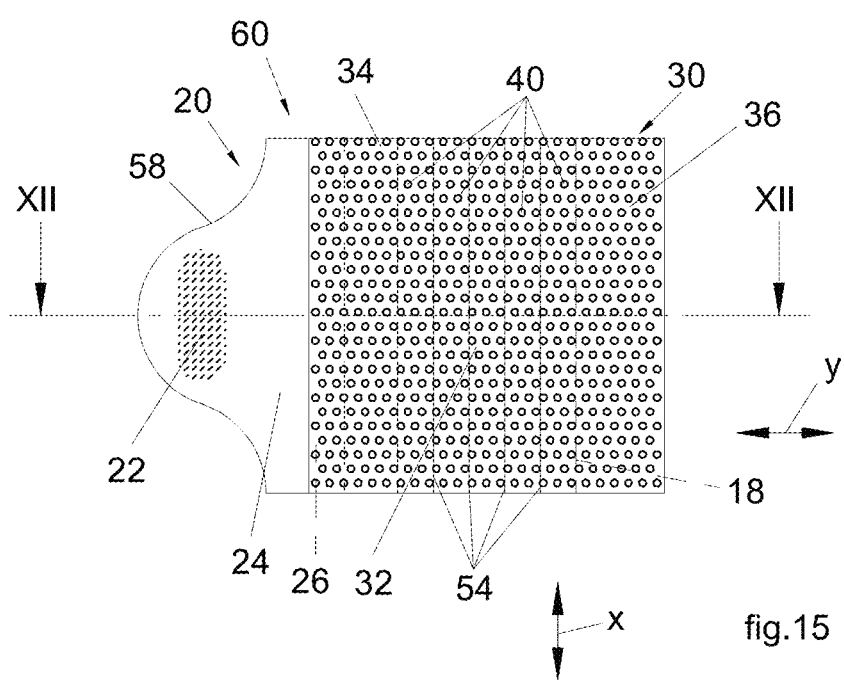
FIG. 15 is a schematic plan view showing an elastic side panel for absorbent sanitary articles in an extended position.

An individual elastic side panel obtained from a transversely extensible continuous elastic laminate 50 is shown in FIG. 15 and is indicated by the reference numeral 60. The elastic side panel 60 is shown in an extended position for a better understanding. FIG. 12, which is a cross-section taken along the line XII-XII of the transversely extensible continuous elastic laminate 50 of FIG. 11, is identical to a cross-section taken along the line XII-XII of the individual elastic side panel 60 of FIG. 15.

With reference to FIGS. 15 and 12, the elastic side panel 60 comprises a first and a second web 10, 30 having respective pleated central portions 12, 34 having respective pleats 52, 54 parallel to a first direction X, and respective first and second non-pleated edge portions 14, 34 and 16, 36 on opposite sides of the pleated central portions 12, 32. An elastic tape 18 is sandwiched between the pleated central portions 12, 32 of the first and second web 10, 30. The elastic tape 18 is elastically stretchable in a second direction Y transversal to the first direction X. The elastic tape 18 is joined to the first and second web 10, 30 by a pattern of spot welds 40.

The elastic side panel 60 comprises a support web 20 of a non-woven material including an edge portion 26 joined to the first non-pleated edge portions 14, 34 by said pattern of spot welds 40. The pattern of spot welds 40 may be reinforced in the area connecting the first non-pleated portions 14, 34 of the first and second web 10, 30 to the edge portion 26 of the support web 20. The edge portion 26 of the support web 30 in the first direction X has the same length as the non-pleated edge portions 14, 34 of the first and second web 10, 30. The support web 20 includes a tab of non-woven material 58 extending from the edge portion 26. The tab 58 has a micro-hook pad 22 integrally formed with the non-woven material forming the tab 58. The planar surface 24 of the tab has a portion which completely surrounds the micro-hook pad 22. The portion of the planar surface 24 which surrounds the micro-hook pad 22 may have a width comprised between 1-10 mm and preferably comprised between 2-7 mm.

Figure 16:
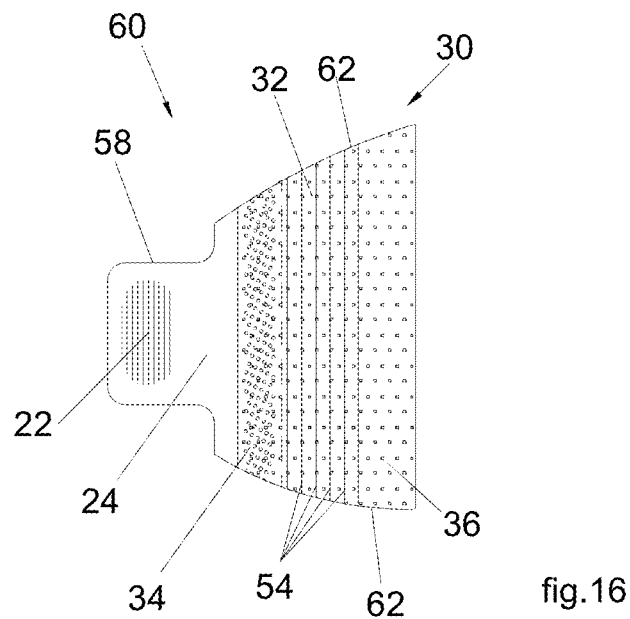
FIG. 16 is a schematic plan view showing an elastic side panel with a different shape.

With reference to FIG. 16, the elastic side panel 60 may have curved flanks 62, which may be formed by cutting the transversely extensible continuous elastic laminate 50 along substantially V-shaped curved cutting lines. The portion of the transversely extensible continuous elastic laminate 50 comprised between each of the two substantially V-shaped curved cutting lines is disposed as scrap.

FIG. 17-20 show a second embodiment of a method for producing a transversely extensible continuous elastic laminate. The elements corresponding to those previously disclosed are indicated by the same reference numbers.

Figure 17:
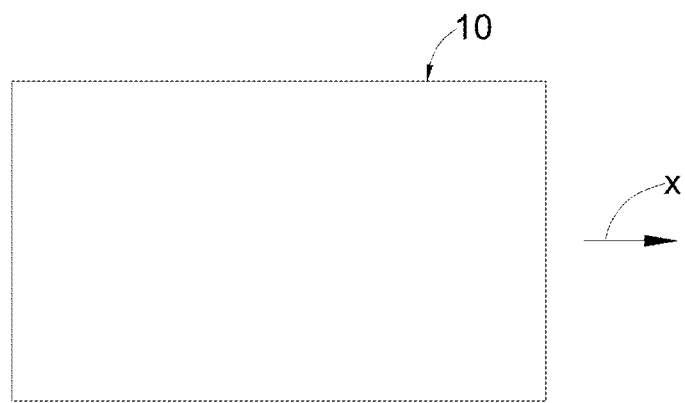
FIGS. 17-20 are schematic plan views showing various steps of a second embodiment of a method for producing a transversely extensible continuous elastic laminate having integral micro-hook pads.

With reference to FIG. 17, a first continuous web 10 is fed in a longitudinal direction X. The first continuous web 10 may be made of a non-woven material.

Figure 18:
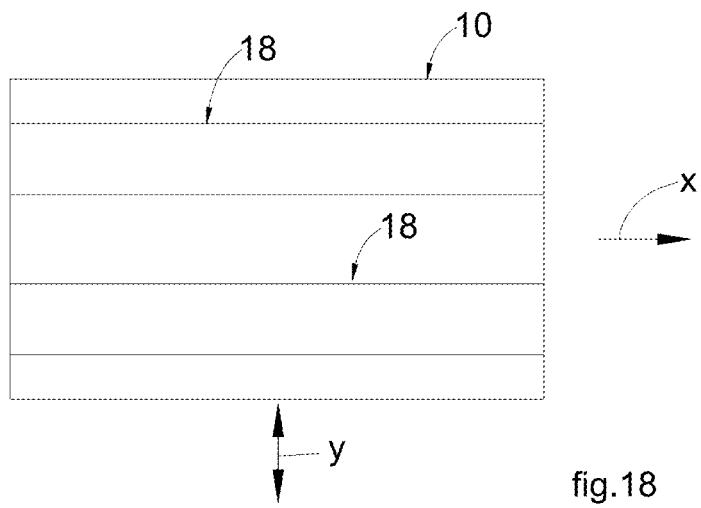

In a second step, shown in FIG. 18, two continuous elastic tapes 18 parallel to each other and spaced apart in a transversal direction Y are fed in the longitudinal direction X and are overlapped to respective portions of the first continuous web 10. The two elastic tapes 18 may be obtained from a single continuous elastic tape unwound from a reel and cut longitudinally so as to form the two separate elastic tapes advancing in the longitudinal direction X.

The two continuous elastic tapes 18 are elastically stretched in the transversal direction Y when they are applied to the continuous web 10. Transverse stretching and retention of the two elastic tapes 18 on the first continuous web 10 are carried out as previously disclosed.

Figure 19:
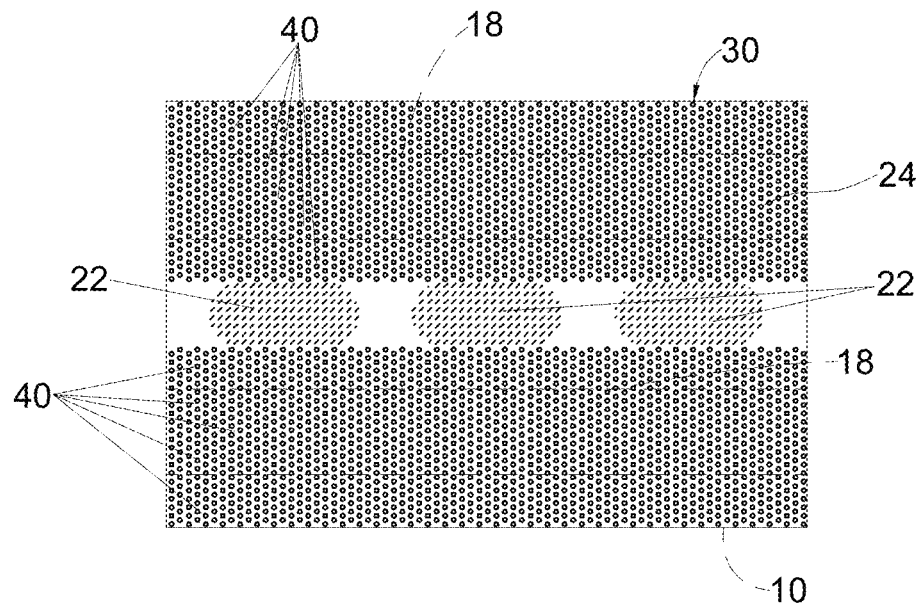

With reference to FIG. 19, a second continuous web of a non-woven material is fed in the longitudinal direction Y and is overlapped to the first continuous web 10.

The second continuous web 30 has a row of micro-hook pads 22 integrally formed in the non-woven material forming the second continuous web 30. The row of micro-hook pads 22 is formed in a central portion of a planar surface 24 of the second continuous web 30 located between the two continuous elastic tapes 18. The micro-hook pads 22 may be formed as previously disclosed.

The two continuous elastic tapes 18 are sandwiched between respective portions of the first and second webs 10, 30.

The first and second web 10, 30, the two elastic tapes 18 are fixed to each other by a pattern of spot welds 40. The spot welds 40 may also extend through the micro-hook pads 22. The elastic tapes 18 are stretched in the transversal direction Y during the spot welding which joins the elastic tapes 18 to the first and second web 10, 30.

Figure 20:
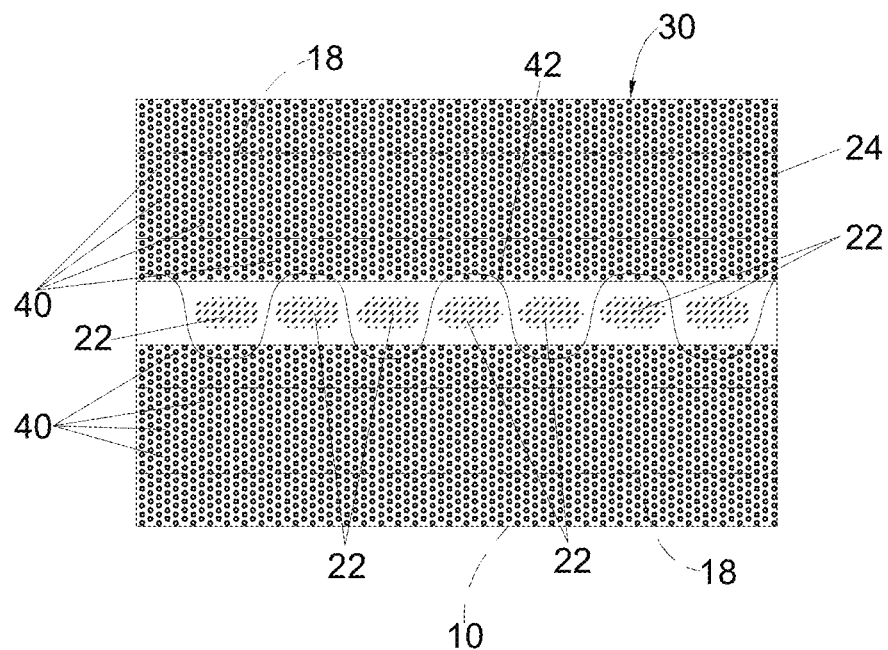

With reference to FIG. 20, the method further comprises a cutting step wherein the first and second webs 10, 30 are cut along a continuous undulated cutting line 42. The cutting line 42 passes between each pair of adjacent micro-hook pads 22 and does not cut the two elastic tapes 18.

Figure 21:
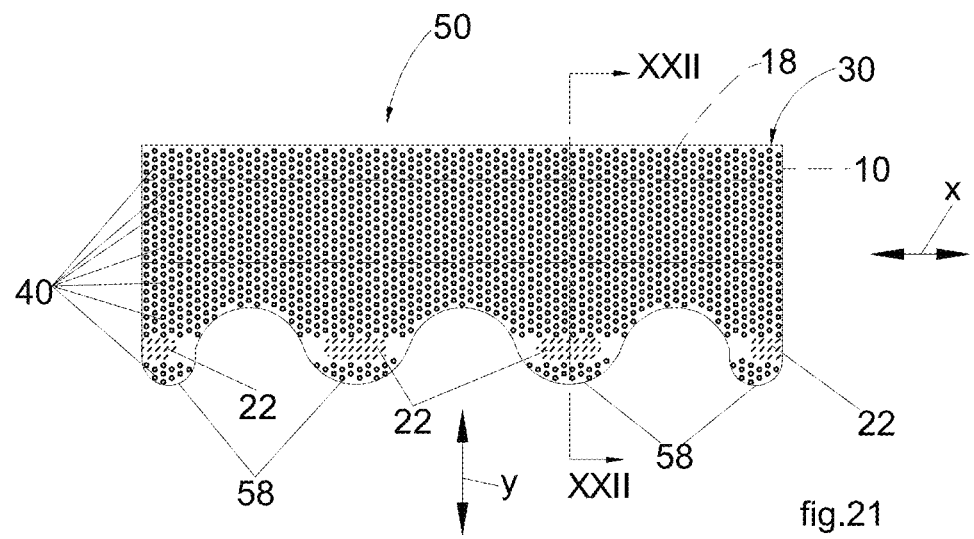
FIG. 21 is a schematic plan view of a second embodiment of a transversely extensible continuous elastic laminate in an extended position.
Figure 22:
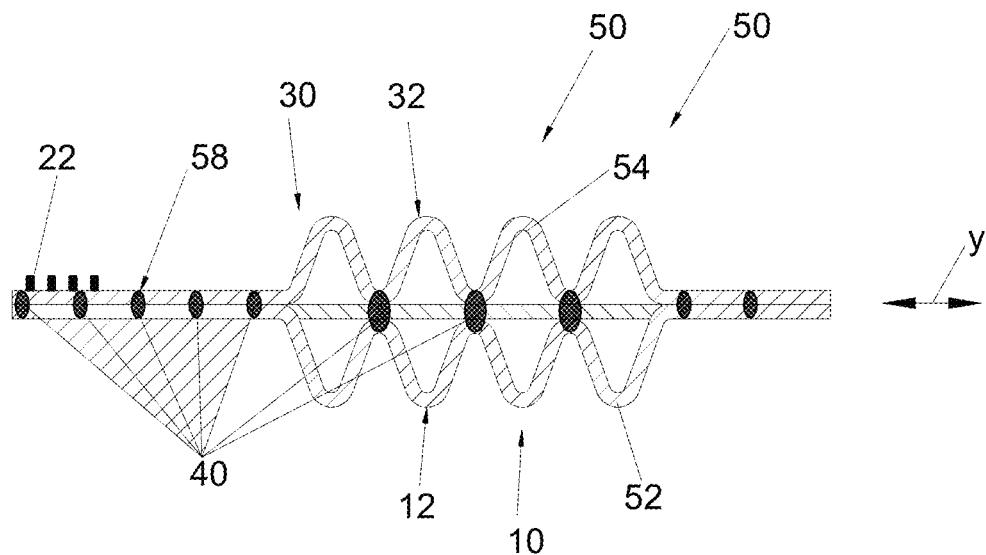
FIG. 22 is a schematic cross-section taken along the line XXII-XXII of FIG. 21, FIGS. 23-29 are schematic plan views showing various steps of a third embodiment of a method for producing a transversely extensible continuous elastic laminate having integral micro-hook pads.

After the cut of the first and second web 10, 30 along the cutting line 42, two separate transversely extensible continuous elastic laminates 50 are formed, each of which has the form shown in FIGS. 21 and 22.

With reference to FIGS. 21 and 22, the transversely extensible continuous elastic laminate 50 comprises a first and a second continuous web 10, 30 extending along a longitudinal direction X and a continuous elastic tape 18 elastically extensible in a transversal direction Y and sandwiched between pleated central portions 12, 32 of the first and second continuous web 10, 30 and joined thereto by a pattern of spot welds 40.

The transversely extensible continuous elastic laminate 50 includes a row of tabs 58 of non-woven material integrally formed with the first and second continuous web 10, 30. The tabs 58 extend in the transverse direction from the pleated central portions 12, and are spaced apart from each other in the longitudinal direction X.

The tabs 58 have respective micro-hook pads 22 integrally formed with the non-woven material forming the second web 30. Each micro-hook pad 22 is completely surrounded by a portion of the planar surface of the second web 30.

The tabs 58 may be folded over the second web 30 along a folding line parallel to the longitudinal axis X, so that the micro-hook pads 22 are releasably fastened to corresponding portions of the second web 30.

The transversely extensible continuous elastic laminate 50 may be cut transversely to form individual elastic side panels as previously disclosed. Each elastic side panel has a respective tab 58 integrally formed with the first and/or second non-woven webs 10, 30 and has a micro-hook pad 22 integrally formed with the non-woven material of one the two non-woven webs. The micro-hook pad 22 is completely surrounded by a portion of the planar surface of one the two non-woven webs.

Each tab 58 may be formed by two webs 10, 30 overlapped and joined to each other by a pattern of spot welds 40. The pattern of spot welds 40 may be reinforced on the tab 58. This structure makes the tab 58 particularly resistant. In a possible embodiment, each tab 58 may be formed by a single web 10 or 30 of non-woven material.

FIG. 23-32 show a third embodiment of a method for producing a transversely extensible continuous elastic laminate. The elements corresponding to those previously disclosed are indicated by the same reference numbers.

Figure 23:
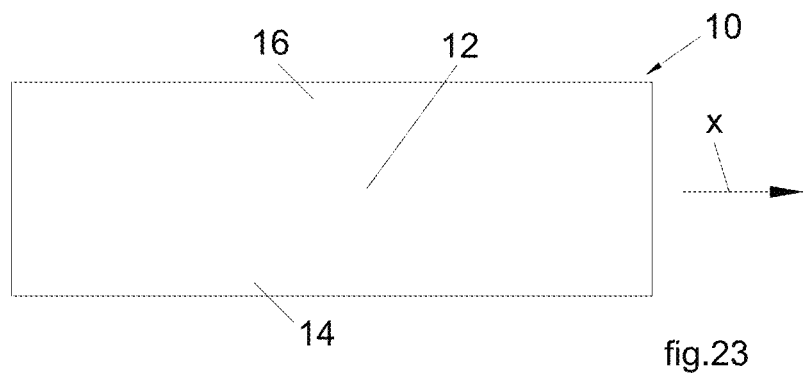

With reference to FIG. 23 a first continuous web 10 is fed in a longitudinal direction X. The first continuous web 10 may be made of a non-woven material. The first continuous webs 10 has a central portion 12 and first and second edge portions 14, 16 opposite to each other with respect to the central portion 12.

Figure 24:
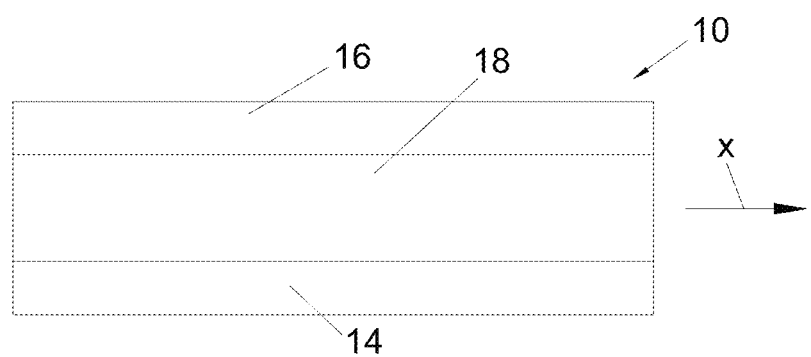

With reference to FIG. 24, a continuous elastic tape is fed in the same longitudinal direction X and is overlapped to the central portion 12 of the first continuous web 10. The elastic tape 18 is elastically stretched in a direction Y transversal to the longitudinal direction X when it is applied to the central portion 12 of the first continuous web 10.

Figure 25:
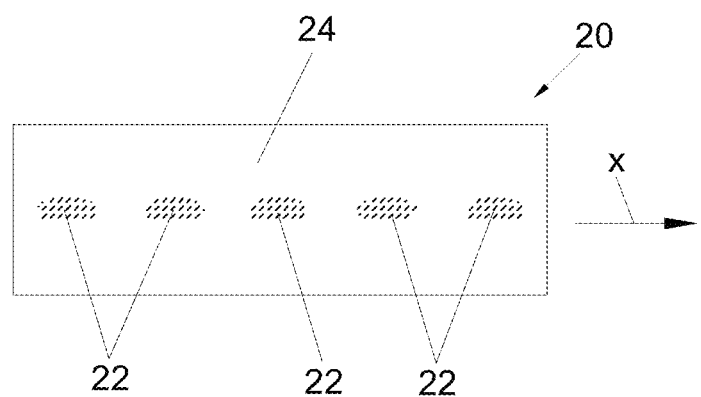

With reference to FIG. 25, the method comprises providing a continuous support web 20 of non-woven material having an integrally formed row of micro-hook pads 22. The row of micro-hook pads 22 may be formed in a central portion of a planar surface 24 of the support web 20. The micro-hook pads 22 may be formed as previously disclosed with reference to FIGS. 4 and 5.

Figure 26:
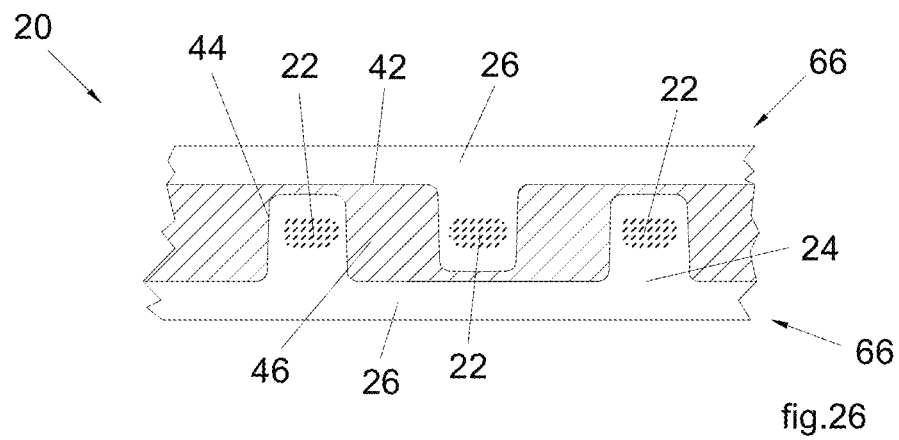

With reference to FIG. 26, the method further comprises a cutting step wherein the continuous support web 20 is cut along two continuous undulated cutting lines 42, 44 passing between each pair of adjacent micro-hook pads 22. The two continuous undulated cutting lines 42, 44 define a continuous undulated strip 46, shown by hatched lines in FIG. 26, comprised between the two cutting lines 42, 44 which is disposed as waste. In a possible embodiment, the continuous support web 20 may be cut along only one continuous undulated cutting line.

Figure 27:
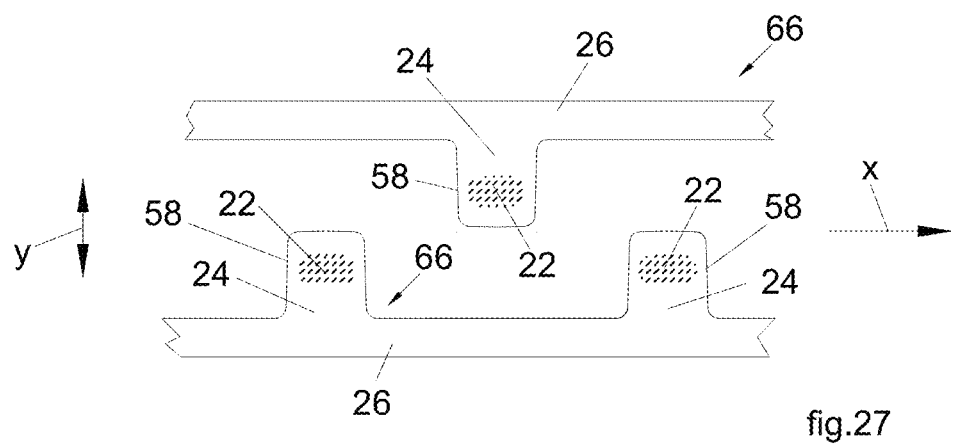

With reference to FIG. 27, after the cut of the support web 20 along the two continuous undulated cutting lines 42, 44 two separate continuous tab chains 66, are formed, which are offset from each other in the longitudinal direction X. The two continuous tab chains 66, comprise respective continuous longitudinal edge portions 26, and respective tabs 58 projecting from the respective continuous longitudinal edge portions 26 in the transversal direction Y. Each tab 58 has a respective micro-hook pad 22 integrally formed on a respective planar surface 24. Each micro-hook pad 22 is completely surrounded by a portion of the planar surface 24. In each continuous tab chain 66 the respective tabs 58 are spaced apart from each other in the longitudinal direction X.

After the cut of the support web 20 along the two continuous undulated cutting lines 42, 44 the two separate continuous tab chains 66 have the respective tabs 58 facing inward with respect to a longitudinal centre line. After the cut, the two separate continuous tab chains 66 are crossed with each other as they advance in the longitudinal direction, in order to bring the two separate continuous tab chains 66 in a position in which the respective tabs 58 face outward with respect to a longitudinal centre line.

Figure 28:
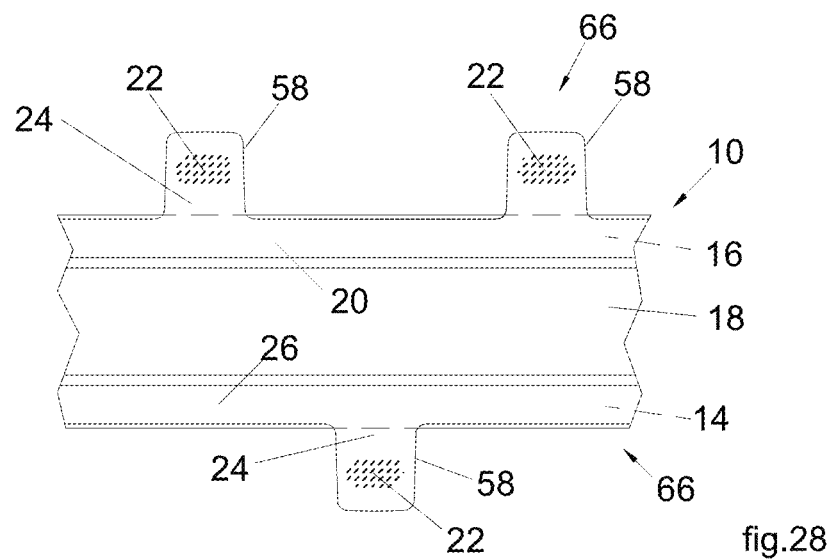

Then, as shown in FIG. 28, the two continuous longitudinal edge portions 26 of the two continuous tab chains 66 are overlapped, respectively, to the first edge portion 14 and to the second edge portion 16 of the first continuous web 10.

Figure 29:
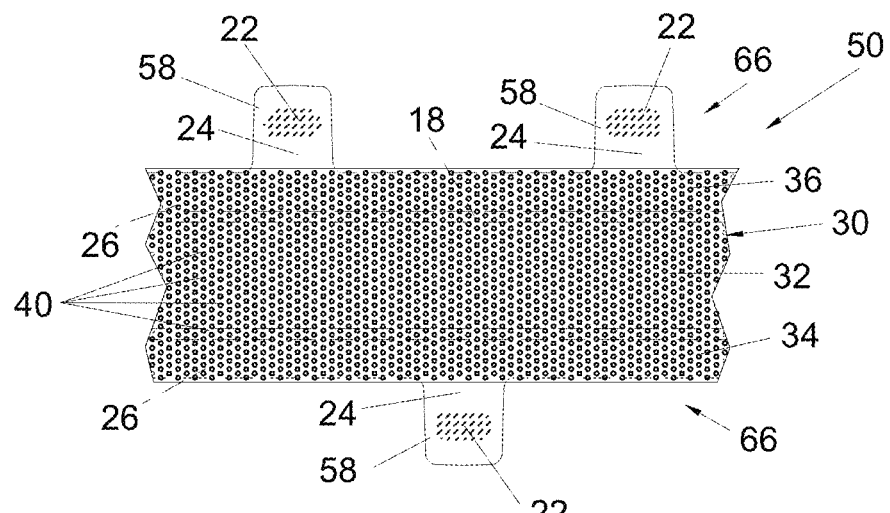

In a further step shown in FIG. 29, a second continuous web 30 is fed in the longitudinal direction X and is overlapped to the first continuous web 10.

The second continuous web 30 may have the same width as the first continuous web 10 and may be made of the same material (e.g. a non-woven material). The second continuous web 30 has a central portion 32 and first and second edge portions 34, 36 opposite to each other with respect to the central portion 12.

The second continuous web 30 is applied over the first continuous web 10 so that the continuous elastic tape 18 is sandwiched between the respective central portions 12, of the first and second webs 10, 30. The continuous longitudinal edge portions 26 of the two continuous tab chains 66 may be sandwiched between respective first edge portions 14, 34 of the first and second continuous web 10, 30 or may be applied on the outer surface of the first or second edge portion 14, 34.

Then, the first and second web 10, 30, the elastic tape 18 and the two continuous longitudinal edge portions 26 of the two continuous tab chains 66 are joined to each other by a pattern of spot welds 40.

After the spot-welding step, a finished transversely extensible continuous elastic laminate 50 is obtained.

The tabs 58 of the two continuous tab chains 66 may be folded over the second web 30 along respective folding lines parallel to the longitudinal axis X, so that the micro-hook pads 22 are releasably fastened to corresponding portions of the second web 30.

Figure 30:
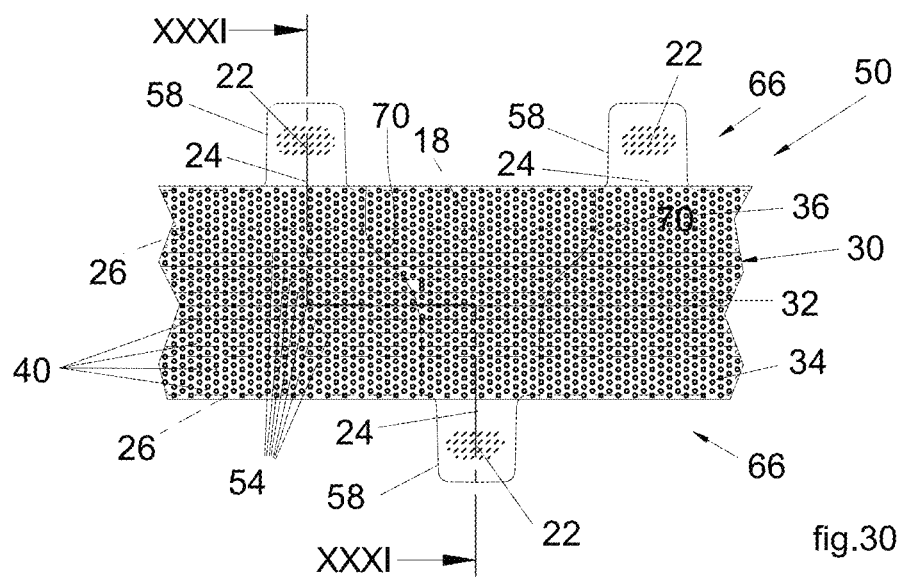
FIG. 30 is a schematic plan view of a third embodiment of a transversely extensible continuous elastic laminate in an extended position.
Figure 31:
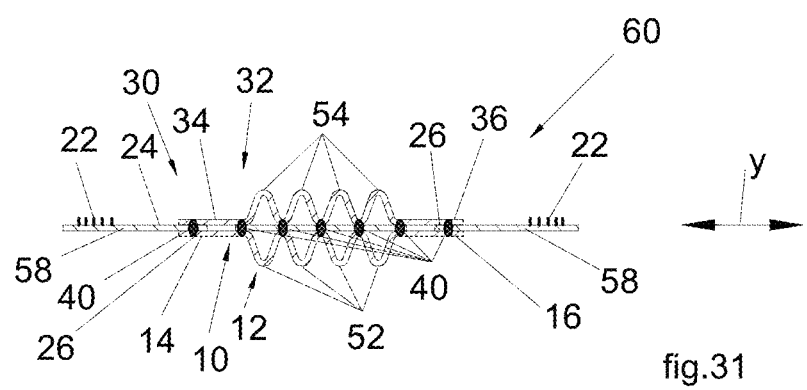
FIG. 31 is a schematic cross-section taken along the line XXXI-XXXI of FIG. 30.

With reference to FIGS. 30 and 31, when the vacuum suction which holds the elastic tape 18 stretched in the transversal direction Y is released, the elastic tape 18 contracts in the transversal direction Y. The transversal contraction of the elastic tape 18 forms longitudinal pleats 52, 54 on the central portions 12, 32 of the first and second continuous web 10, 30. The edge portions 14, 34 and 16, 36 of the first and second continuous webs 10, 30 which extend transversally beyond the elastic tape 18 remain non-pleated.

With reference to FIGS. 30 and 31, the transversely extensible continuous elastic laminate 50 obtained by the method previously disclosed comprises a first and second continuous web 10, 30 overlapped to each other and extending along a longitudinal direction X. The first and second continuous web 10, 30 have respective pleated central portions 12, 32 having longitudinal pleats 52, 54 and respective first and second non-pleated edge portions 14, 34 and 16, 36.

A continuous elastic tape 18 elastically extensible in a transverse direction Y is sandwiched between the pleated central portions 12, 32 of the first and second continuous webs 10, 30 and joined thereto by a pattern of spot welds 40.

The transversely extensible continuous elastic laminate 50 comprises a first and a second tab chain 66 of non-woven material having respective continuous longitudinal edge portions 26 and respective rows of tabs 58 having respective micro-hook pads 22 integrally formed with the non-woven material of the tabs 58.

In each tab chain 66 the respective tabs 58 are spaced apart from each other in the longitudinal direction X. The tabs 58 of the two tab chains 66 are offset with respect to each other.

The continuous longitudinal edge portions 26 of the first and second tab chains 66 are joined to the respective first and second non-pleated edge portions 14, 34 and 16, 36 of the first and second continuous web 10, 30 by said pattern of spot welds 40. The pattern of spot welds 40 may be reinforced in the areas joining the continuous longitudinal edge portions 26 of the first and second tab chain 66 and the respective first and second non-pleated edge portions 14, 34 and 16, 36 of the first and second continuous web 10, 30.

In a possible embodiment, the micro-hook pads 22 of the first and second tab chain 66 may have respective hooks oriented in opposite direction to each other.

The transversely extensible continuous elastic laminate 50 may be cut along cutting lines 70 (FIG. 30) for forming individual elastic side panels 60, as previously disclosed.

An absorbent sanitary article may have an absorbent central body and two or four elastic side panels 60 as previously described fixed to two opposite longitudinal edges of said central body.

As compared to the prior art disclosed in EP-A-3213728, the elastic side panels 60 according to the present invention have an increased resistance and are less exposed to the risk of breaks because the tabs 58 are connected to the webs 10, 30 along the whole length of the webs 10, 30.

In use, the tabs 58 have a soft feeling to the touch because the micro-hook pads 22 are completely surrounded by a portion of non-woven material which is softer than the relatively rigid thermoplastic material forming the micro-hook pads of the prior art.

The method for manufacturing the transversely extensible continuous elastic laminate 50 does not require the application of discrete tabs on the edges of the elastic laminate. The tabs with the respective micro-hook pads 22 are formed by applying and cutting a continuous web. This involves considerable advantages in that there is no need for complex and expensive repitch devices for applying discrete elements at a constant pitch.

Of course, without prejudice to the principle of the invention, the details of construction and the embodiments can be varied, even significantly, with respect to those illustrated here without departing from the scope of the invention as defined by the following claims.

The invention claimed is:

1. A method for producing a continuous transversely extensible elastic laminate comprising:
    feeding in a longitudinal direction two first continuous webs, the two first continuous webs being spaced from each other in a transverse direction and having respective central portions and respective first and second edge portions on opposite sides of the respective central portions,
    feeding in said longitudinal direction two continuous elastic tapes,
    elastically stretching said two continuous elastic tapes in the transverse direction relative to said longitudinal direction, and applying said two continuous elastic tapes to respective central portions of said two first continuous webs while stretched in said transversal direction,
    feeding in said longitudinal direction a continuous support web of a non-woven material having two continuous edge portions, the continuous support web having a row of micro-hook pads integrally formed in the non-woven material forming said continuous support web,
    applying said two continuous longitudinal edge portions of said continuous support web to respective first edge portions of said two first continuous webs,
    feeding in said longitudinal direction two second continuous webs spaced from each other in said transverse direction and having respective central portions and respective first and second edge portions on opposite sides of the respective central portions,
    applying said two second continuous webs to respective first continuous webs and sandwiching said two continuous elastic tapes between respective central portions of said first and second continuous webs,
    joining to each other said two first and second webs, said two elastic tapes and the edge portions of the continuous support web by a pattern of spot welds while said two elastic tapes are stretched in said transversal direction, and
    cutting the continuous support web along at least one continuous undulated cutting line passing between each pair of adjacent micro-hook pads of the row of micro-hook pads so as to form two separate continuous transversely extensible elastic laminates.

2. The method of claim 1, wherein said at least one continuous undulated cutting line forms in each of said continuous transversely extensible elastic laminates a row of tabs connected to each other by a respective continuous longitudinal edge portion and spaced apart from each other in said longitudinal direction.

3. The method of claim 1, wherein said row of micro-hook pads is integrally formed in said non-woven material by locally liquifying or fluidifying the non-woven material and inserting the liquified or fluidified non-woven material into cavities of a molding roller.

4. The method of claim 3, wherein locally liquifying or fluidifying the non-woven material is obtained by subjecting the non-woven material to ultrasonic compression or to thermomechanical compression.

5. A method for producing a continuous transversely extensible elastic laminate comprising:

feeding in a longitudinal direction a first continuous web having a central portion and first and second edge portions on opposite sides of the central portion, feeding in said longitudinal direction a continuous elastic tape, elastically stretching said continuous elastic tape in a transverse direction relative to said longitudinal direction, and applying said continuous elastic tape to the central portion of said first continuous web while stretched in said transversal direction, feeding in said longitudinal direction a continuous support web of a non-woven material having a row of micro-hook pads integrally formed in the non-woven material forming said continuous support web, cutting the continuous support web along at least one continuous undulated cutting line passing between each pair of adjacent micro-hook pads of the row of micro-hook pads so as to form two separate continuous tab chains from the continuous support web, each of the two continuous tab chains having a continuous longitudinal edge portions on one side and tabs having respective integral micro-hook pads on the other opposite side, applying said two continuous longitudinal edge portions of said two continuous tab chains to respective first and second edge portions of said first continuous web, feeding in said longitudinal direction a second continuous web having a central portion and first and second edge portions on opposite sides of the central portion, applying said second continuous web to the first continuous web and sandwiching said continuous elastic tape between respective central portions of said first and second continuous webs, and joining to each other said first and second continuous webs, said elastic tape and said two continuous longitudinal edge portions of said two continuous tab chains by a pattern of spot welds.

6. The method of claim 5, wherein said row of micro-hook pads is integrally formed in said non-woven material by locally liquifying or fluidifying the non-woven material and inserting the liquified or fluidified non-woven material into cavities of a molding roller.

7. The method of claim 6, wherein locally liquifying or fluidifying the non-woven material is obtained by subjecting the non-woven material to ultrasonic compression or to thermomechanical compression.

* * * * *

UNITED STATES PATENT AND TRADEMARK OFFICE
CERTIFICATE OF CORRECTION

| | | |
|---|---|---|
| PATENT NO. | : 12,207,992 B2 | Page 1 of 1 |
| APPLICATION NO. | : 17/696998 | |
| DATED | : January 28, 2025 | |
| INVENTOR(S) | : Diego Gualtieri and Alessandro Cipriani | |

It is certified that error appears in the above-identified patent and that said Letters Patent is hereby corrected as shown below:

On the Title Page

Item (71) Applicant address information should be listed as:
- Fameccanica.Data S.p.A., San Giovanni Teatino (Chieti), ITALY -

Item (72) Inventor address information should be listed as:
- Diego GUALTIERI, San Giovanni Teatino (Chieti), ITALY
Alessandro CIPRIANI, San Giovanni Teatino (Chieti), ITALY -

Signed and Sealed this
First Day of April, 2025

Coke Morgan Stewart
*Acting Director of the United States Patent and Trademark Office*